United States Patent [19]

Jackson

[11] Patent Number: 5,569,798
[45] Date of Patent: Oct. 29, 1996

[54] CHLORINATION OF HALOGENATED CARBON COMPOUNDS FOR PURIFICATION PURPOSES

[75] Inventor: Andrew Jackson, Baton Rouge, La.

[73] Assignee: LaRoche Industries, Inc., Baton Rouge, La.

[21] Appl. No.: 423,080

[22] Filed: Apr. 17, 1995

[51] Int. Cl.$^6$ .............................. C07C 17/38; C07C 17/04
[52] U.S. Cl. .......................... 570/178; 570/177; 570/179; 570/247
[58] Field of Search .................................... 570/177, 179, 570/178, 247

[56] References Cited

U.S. PATENT DOCUMENTS

| | | |
|---|---|---|
| 2,498,552 | 2/1950 | Kilgren et al. . |
| 3,696,156 | 10/1972 | Weeks . |
| 4,034,049 | 7/1977 | Lovelace . |
| 4,329,323 | 5/1982 | Shiozaki et al. . |
| 4,754,088 | 6/1988 | Schmidhammer . |
| 4,922,042 | 5/1990 | Hoos et al. . |
| 4,948,479 | 8/1990 | Brooks et al. . |
| 5,105,035 | 4/1992 | Wang et al. . |
| 5,300,714 | 5/1994 | Pothapragada et al. . |

FOREIGN PATENT DOCUMENTS

| | | |
|---|---|---|
| 0420709 | 4/1991 | European Pat. Off. . |
| 370688 | 7/1994 | European Pat. Off. . |
| 54-19902 | 2/1979 | Japan . |
| 86387 | 7/1970 | Netherlands . |
| 685657 | 9/1979 | Russian Federation . |
| 627773 | 8/1949 | United Kingdom . |
| 1186742 | 4/1970 | United Kingdom . |

OTHER PUBLICATIONS

Ayscough, P. B. et al, "Photochlorination Studies", 1966, pp. 1838–1845.

Poutsma, M. L. et al, "Chlorination Studies of Unsaturated Materials in Nonpolar Media. I. Solvent Effects on Radical Addition of Chlorine to Chloroethylenes", Union Carbide Research Institute, Union Carbide Corp., Tarrytown, NY, Sep. 20, 1964, pp. 3807–3814.

Mortimer Chem A conceptual Approach (1968) pp. 446, 447.

*Primary Examiner*—Alan Siegel
*Attorney, Agent, or Firm*—Andrew Alexander

[57] ABSTRACT

A method of chlorinating vinylidene chloride contained in a solution 1,1-dichloro-1-fluoroethane to provide a chlorinated compound having a boiling point different from the 1,1-dichloro-1-fluoroethane to permit separation therefrom, the method comprising providing a solution containing 1,1-dichloro-1-fluoroethane and vinylidene chloride; and contacting said solution with chlorine and an alumina catalyst to effect chlorination of said vinylidene chloride to produce a chlorinated compound having a boiling point different than said 1,1 dichloro-1-fluoroethane.

27 Claims, No Drawings

CHLORINATION OF HALOGENATED CARBON COMPOUNDS FOR PURIFICATION PURPOSES

BACKGROUND OF THE ART

This invention relates to a method of purifying 1,1-dichloro-1-fluoroethane by removal of unsaturated carbon compounds such as vinylidene chloride having the same or similar boiling points.

In the prior art, 1,1-dichloro-1-fluoroethane, sometimes referred to by the designation HCFC-141b, has been prepared by the reaction of vinylidene chloride with hydrogen fluoride. Often after the reaction, traces of unreacted vinylidene chloride, as well as various other unsaturated organic impurities, remain in the 1,1-dichloro-1-fluoroethane and cannot be easily separated therefrom by distillation or other means because they have similar boiling points. Vinylidene chloride has a boiling point of 31.7° C. and 1,1-dichloro-1-fluoroethane has a boiling point of 32.1° C., and thus they are difficult to separate by distillation. It is particularly desirable to remove vinylidene chloride because it is toxic and is considered to be a carcinogen.

Various methods have been proposed for removing unsaturated organic compounds, such as vinylidene chloride from saturated hydrohalofluorocarbons. For example, U.S. Pat. No. 5,105,035 discloses a process for removing vinylidene chloride and other unsaturated impurities film HCFC-141b by reaction with hydrogen over a catalyst such as palladium on alumina. However, this process can result in a loss of HCFC-141b by dechlorination which results from excessive hydrogenation and hydrodechlorination.

U.S. Pat. No. 5,300,714 discloses a method of removing olefinic impurities, such as perfluoroisobutylene, from fluoroperhalocarbon liquid, such as perfluorinated liquid. The method comprises the step of contacting the fluoroperhalocarbon liquid with a body of particles comprising particles selected from the group consisting of alumina, alkali alumina, alkali metal hydroxide, alkaline earth oxide, alkaline earth hydroxide, silicon oxide, tin oxide, zinc oxide, alkaline earth basic carbonate, and alkaline earth basic phosphate, transition alumina particles and mixtures thereof.

European Patent 39311839 (1989) discloses purification of saturated fluorohalocarbons containing unsaturated impurities by the use of aluminas to oxidize unsaturated impurities to carbon dioxide.

U.S. Pat. No. 4,754,088 discloses a process for oxychlorination of ethylene wherein 1,2-dichloroethane is prepared by chlorination of ethylene-containing reaction vent gases from the oxychlorination of ethylene in the presence of a catalyst carrier impregnated with metal compounds wherein the waste from the oxychlorination stage are chlorinated, the improvement comprising preheating the ethylene-containing waste gases to at least 50° C. and then chlorinating the ethylene at 100° to 300° C. at a pressure of 1 to 7 bar with a space velocity of 100 to 5000 h$^{-1}$ related to standard conditions in the presence of at least one metal compound selected from the group consisting of chlorides and oxides of manganese, nickel and cobalt supposed on a catalyst carrier with reduced formation of oxychlorinated by-products.

U.S. Pat. No. 4,329,323 discloses a process for removing ethylene and vinyl chloride from a gas stream containing them by passing a mixed gas containing ethylene, vinyl chloride and a necessary amount of chlorine through a fixed-bed reactor charged with, as a catalyst, an activated alumina supporting at least 4% by weight of chloride in terms of iron, the catalyst having an outer surface area per unit packed catalyst volume of not less than 7.8 cm$^2$/ml. Ethylene and vinyl chloride are converted into and removed as 1,2-dichloroethane and 1,1,2-trichloroethane. The concentrations of ethylene and vinyl chloride can be decreased to not more than 10 ppm and not more than 20 ppm, respectively.

U.S. Pat. No. 2,498,552 discloses a process for the chlorination of normally gaseous paraffinic hydrocarbons which comprises introducing the hydrocarbon to be chlorinated and chlorine into a chlorination zone, introducing cupric oxychloride into the chlorination zone, maintaining a temperature within the range of from about 325° C. to about 500° C. in the chlorination zone, regulating the rate of introduction of the cupric oxychloride so that at least one mole of oxychloride is introduced per mole of chlorine introduced thereto, and recovering the chlorinated hydrocarbons from the gaseous effluent from the chlorination zone.

U.S. Pat. No. 4,034,049 discloses meso-1,2,3,4-tetrachlorobutane produced in an improved liquid phase chlorination process wherein the trans-1,4-dichlorobutene-2 is contacted with chlorine in the presence of a catalytic amount of molybdenum.

U.S. Pat. No. 4,922,042 discloses a process for the production of 1,2-dichloroethane by the reaction between ethylene and chlorine in the vapor phase in the presence of a catalyst comprising alumina, wherein the reaction is carried out using a fluidized bed comprising fluidizable, substantially spherical particles of alumina of surface area not exceeding 10 m$^2$g$^{-1}$ and especially in the range 0.2 to 6 m$^2$g$^{-1}$.

British Patent 627,773 (1949) discloses the separation of 1,1-dichloro-1-fluoroethane from its admixture with vinylidene chloride by chlorination of the vinylidene chloride and recovery of the 1,1-dichloro-1-fluoroethane by distillation.

Poutsma et al in an article entitled "Chlorination Studies of Unsaturated Materials in Nonpolar Media. I. Solvent Effects on Radical Addition of Chlorine to Chloroethylenes" disclose that the relative rates of addition of chlorine atom to 1,1-dichloroethylene, cis- and trans-1,2-dichloroethylene, trichloroethylene, and tetrachloroethylene in noncomplexing solvents have been measured both directly by competitive photochlorination of pairs of olefins and indirectly by comparison of addition to each olefin in competition with hydrogen abstraction from cyclohexane. The selectivity of chlorine atom with respect to such radical addition has been found to be substantially increased by the presence of the complexing solvents benzene and carbon disulfide. Solvent dependence has also been demonstrated for the competition between addition to the olefins and hydrogen abstraction from cyclohexane; attempts to extend such solvent effects to competitive addition and abstraction behavior of the trichloromethyl radical were unsuccessful.

In spite of these prior processes, there is still a great need for an economic, efficient process that enables separation of vinylidene chloride, for example, from 1,1-dichloro-1-fluoroethane. The present invention provides such a process.

SUMMARY OF THE INVENTION

It is an object of this invention to provide a process for purifying 1,1-dichloro-1-fluoroethane.

It is another object of this invention to provide an improved process for chlorination of vinylidene chloride contained in 1,1-dichloro-1-fluoroethane.

It is yet another object of this invention to provide an improved process for converting vinylidene chloride to a saturated compound that has a boiling point sufficiently different from 1,1-dichloro-1-fluoroethane to permit separation thereof from 1,1-dichloro-1-fluoroethane by distillation, for example.

These and other objects will become apparent from the specification and claims appended hereto.

In accordance with these objects, there is provided a method of chlorinating vinylidene chloride contained in a solution 1,1-dichloro-1-fluoroethane to provide a chlorinated compound having a boiling point different from the 1,1-dichloro-1-fluoroethane to permit separation therefrom. The method comprises providing a solution containing 1,1-dichloro-1-fluoroethane and vinylidene chloride; introducing chlorine to the solution to provide chlorine in the solution; and contacting the chlorine and the solution with an alumina catalyst to effect chlorination of the vinylidene chloride to produce one of 1,1,1,2-tetrachloroethane and trichloroethylene. The 1,1 dichloro-1-fluoroethane is useful as a foam blowing agent and as a solvent in various applications.

DETAILED DESCRIPTION OF PREFERRED EMBODIMENTS

When 1,1-dichloro-1-fluoroethane is produced by reaction of vinylidene chloride or trichloroethane with hydrogen fluoride, the 1,1-dichloro-1-fluoroethane can contain up to 9000 ppm or higher residual vinylidene chloride. Other by-products may be present in lesser amounts; however, it is particularly important to remove vinylidene chloride because of its toxicity. 1,1-dichloro-1-fluoroethane has been found useful as a replacement for trichlorofluoromethane as a foam blowing agent and such use requires that it be substantially free of toxic vinylidene chloride. That is, the level of vinylidene chloride should be reduced to not more than 200 ppm, preferably less than 100 ppm.

In the process of the invention, vinylidene chloride and other unsaturated compounds are chlorinated. When vinylidene chloride is chlorinated, it reacts to produce 1,1,1,2-tetrachloroethane and trichloroethylene. 1,1,1,2-tetrachloroethane has a boiling point of 130.5° C. and trichloroethylene has a boiling point of 88° C. Because these compounds have boiling points substantially different from 1,1 dichloro-1-fluoroethane, (boiling point 32.1° C.), they can be easily separated from 1,1 dichloro-1-fluoroethane by distillation, for example. It should be noted that unsaturated organic compounds other than vinylidene chloride may be chlorinated in a similar way to provide the saturated equivalents.

In the process of the present invention, 1,1-dichloro-1-fluoroethane in the liquid phase containing vinylidene chloride can be contacted with chlorine in the presence of an alumina catalyst. For purposes of contacting, 1,1-dichloro-1-fluoroethane may be present in the liquid phase.

In the present invention, a body of 1,1-dichloro-1-fluoroethane containing vinylidene chloride and other unsaturated organic compounds is first contacted with chlorine to provide chlorine for chlorination in accordance with the invention. The chlorine is added in an amount sufficient to chlorinate vinylidene chloride and other unsaturated compounds in the 1,1-dichloro-1-fluoroethane.

In the present invention, chlorine is preferably added to the 1,1-dichloro-1-fluoroethane solution to provide a molar ratio in the range of about 1:1 to 5:1, chlorine to vinylidene chloride in the solution. Preferably, the chlorine is provided in excess of the vinylidene chloride to permit other unsaturated impurities to be reacted. Also preferably for shorter chlorination times, the chlorine to vinylidene chloride mole ratio is greater than 2.5:1. Further, preferably, the chlorine is added at about ambient temperature and further, preferably, the chlorine is added in gaseous foden for ease of metering.

After chlorine has been added to the 1,1-dichloro-1-fluoroethane solution, the combination is contacted with alumina particles. The alumina particles are effective in catalyzing the chlorination of the vinylidene chloride and other unsaturated compounds to provide saturated compounds with boiling points substantially different from that of 1,1-dichloro-1-fluoroethane.

For purposes of chlorination, the catalytic reaction can be carried out in a temperature range of about 0° to 100° C. and preferably in a temperature range of 10° to 60° C. However, while these temperatures are provided as guides, any temperature may be used which effectively permits chlorination to the equivalent saturated compound. Thus, for purposes of chlorination, a stream of chlorine treated 1,1-dichloro-1-fluoroethane is introduced to the alumina catalyst in these temperature ranges.

While the stream of chlorine treated 1,1-dichloro-1-fluoroethane can be substantially free of water, it is preferred that water be added to the stream to provide a water concentration of less than 3000 ppm and preferably in the range of about 20 to 2000 ppm. However, the amount of water present should be controlled to avoid blocking active sites in the alumina catalyst that promote the chlorination process.

In a preferred embodiment of the invention, the alumina catalyst is treated or saturated with chlorine prior to contacting the catalyst with the 1,1-dichloro-1-fluoroethane containing vinylidene chloride. By pretreating the catalyst with chlorine, the chlorination process is more efficient by providing chlorine more readily available for reaction. The alumina catalyst may be contacted with a fluid containing chlorine for treatment purposes. For example, the treatment may be carried out by contacting the alumina catalyst with 1,1-dichloro-1-fluoroethane saturated with chlorine.

The alumina catalyst can comprise alumina trihychate, pseudoboehmite, alpha alumina monohydrate, and thermal activated aluminas having gamma, eta, chi-rhoeta, delta or kappa structures. The aluminas suitable for catalysts have a surface area of greater than 80 $m^2/gm$ and preferably have a surface area in the range of 100 to 350 $m^2/gm$. Further, preferably, the alumina catalysts have a pore volume in the range of 0.3 to 1 $cm^3/gm$. Alumina catalysts useful in the present invention are available from LaRoche Industries, Inc., Baton Rouge, La., under the designation LaRoche A-204-4®, A-201® and A-203-C1®.

In another embodiment, the alumina catalyst may be doped with alkali and/or alkaline earth metal or metal oxides. Representative of the alkali earth metals that are suitable are lithium, sodium, potassium, rubidium and cesium. The alumina catalyst may be doped by dissolving a soluble from of the alkali and/or alkaline earth metal in an aqueous solution and spraying the alumina particles to deposit alkali and/or alkaline earth metal thereon. When alkali and/or alkaline each metal oxide is used in combination with the alumina, the combination comprises 0.5 to 30 wt. % alkali and/or alkaline metal oxide, preferably 1 to 10 wt. % alkali and/or alkaline metal oxide.

While the inventors do not wish to be bound by any theory of invention and while they do not fully understand the process of chlorination of the invention, it is believed that the schemes for chlorinating vinylidene chloride in 1,1-dichloro-1-fluoroethane in accordance with the invention using alumina catalysts are as follows:

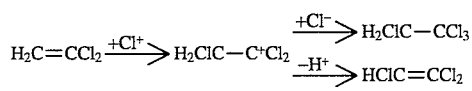

The alumina catalysts used for catalytic purposes are preferably provided in either spherical or granular configuration. Preferably, the alumina particles are provided in a bed through which the combination of chlorine and 1,1-dichloro-1-fluoroethane can be suitably passed through. Thus, the alumina particles are provided in a particle size in the range of 1 µm to 3 mm.

In the present invention, the flow rate of 1,1-dichloro-1-fluoroethane and the bed of alumina catalysts should be constructed to provide a residence time in the range of 5 to 60 minutes with typical residence time of 15 to 25 minutes having been found to be suitable.

In addition, while chlorine is preferably mixed with 1,1-dichloro-1-fluoroethane prior to being introduced to the bed, it will be understood that the chlorine may be introduced to the 1,1-dichloro-1-fluoroethane just prior to being introduced to the bed of metal oxide catalyst. Or, the chlorine can be added to the bed independent of the 1,1-dichloro-1-fluoroethane. Further, the bed comprising metal oxide catalyst, 1,1 -dichloro-1-fluoroethane and chlorine may be kept under pressure effect chlorination.

The following examples are still further illustrative of the invention.

EXAMPLE 1

To test the effectiveness of alumina to effect reaction of chlorine with vinylidene chloride in a 1,1-dichloro-1-fluoroethane solution, a glass column 0.5 inch ID and 3 inches long was filled with activated alumina available from LaRoche Industries, Inc., Baton Rouge, La. under the designation A-201, A-203 and A204-4. The alumina was conditioned with chlorine by passing 1,1-dichloro-1-fluoroethane containing 1 wt. % chlorine through the catalyst for a period of about 1 to 2 hours. Then, 10.775 moles of 1,1-dichloro-1-fluoroethane containing 0.025 moles of vinylidene chloride was treated with 0.05 moles of chlorine and the combination was passed through the column for a period to provide a residence time of 20 minutes. The solution was then treated with sodium sulfite to remove excess chlorine. Thereafter, the solutions were analyzed by gas-liquid chromatography with a detection limit of 1 ppm and results reported as area%. The effectiveness of the different alumina catalysts in the chlorination of vinylidene chloride is shown in the Table where the amount of vinylidene chloride is reported "before" chlorination and "after" chlorination.

TABLE

| Sample | Before* | After* |
|---|---|---|
| A-201 ® | 0.54 | none found |
| A-204-4 ®[1] | 0.16 | none found |
| A-203-Cl ®[2] | 0.16 | none found |

*values given as area % (detection limit 1 ppm)
[1]LaRoche type activated alumina containing ~4% sodium
[2]LaRoche type activated alumina containing ~6% calcium It will be seen from the Table that these catalysts were effective in converting vinylidene chloride to a saturated compound

EXAMPLE 2

This example was performed the same as Example 1 except the test was run to examine catalyst activity over an extended period. Thus, a four liter sample of 1,1 dichloro -1 fluoroethane containing 0.025 moles of vinylidene chloride and 0.05 moles chlorine were passed through beds of A-203-Cl® and A-202-4®, respectively, for 20 minutes residence time. In both cases, vinylidene chloride was consistently reduced below the 20 ppm level throughout a 30-day period.

It will be seen from the above examples that the alumina was effective in the chlorination of vinylidene chloride in a 1,1 dichloro -1-fluoroethane solution.

While the invention has been described in terms of preferred embodiments, the claims appended hereto are intended to encompass other embodiments which fall within the spirit of the invention.

What is claimed is:

1. A method of chlorinating vinylidene chloride contained in a solution 1,1-dichloro-1-fluoroethane to provide a chlorinated compound having a boiling point different from the 1,1-dichloro-1-fluoroethane to permit separation therefrom, the method comprising:

(a) providing a solution containing 1,1-dichloro-1-fluoroethane and vinylidene chloride; and (b) contacting said solution with chlorine and an alumina catalyst having a surface area of at least 80 m²/gm to effect chlorination of said vinylidene chloride to produce a chlorinated compound having a boiling point different than said 1,1 dichloro-1-fluoroethane.

2. The method in accordance with claim 1 including introducing chlorine to said solution prior to said contacting.

3. The method in accordance with claim 2 including adding chlorine to said solution in a mole ratio of 1:1 to 3:1 chlorine to vinylidene chloride.

4. The method in accordance with claim 1 including contacting effected in a temperature range of 0° to 100° C.

5. The method in accordance with claim 1 including contacting effected in a temperature range of 10° to 60° C.

6. The method in accordance with claim 1 including adding chlorine to said solution in a mole ratio of greater than 2.5:1 chlorine to vinylidene chloride.

7. The method in accordance with claim 1 including conditioning said alumina prior to effecting chlorination by treating said alumina with chlorine.

8. The method in accordance with claim 7 including conditioning said alumina by contacting with a 1,1-dichloro-1-fluoroethane solution containing chlorine.

9. The method in accordance with claim 1 wherein said vinylidene chloride in said solution is reduced to less than 200 ppm.

10. The method in accordance with claim 1 wherein said vinylidene chloride in said solution is reduced to less than 100 ppm.

11. The method in accordance with claim 1 wherein said contacting is for a period of less than 2 hours.

12. The method in accordance with claim 1 wherein said alumina has a surface area in the range of 80 to 350 m²/gm.

13. The method in accordance with claim 1 wherein said alumina is doped with at least one alkali or alkaline earth metal oxide.

14. The method in accordance with claim 1 wherein said alumina has an average particle size in the range of 1 μm to 3 mm.

15. A method seperating vinylidene chloride from a 1,1-dichloro-1-fluoroethane solution comprising the steps of:
   (a) providing a solution of 1,1-dichloro-1-fluoroethane containing vinylidene chloride;
   (b) adding chlorine to said solution to provide a chlorine containing solution;
   (c) passing said chlorine containing solution through a bed comprised of alumina particles having a surface area of at least 80 $m^2/gm$ to effect chlorination of said vinylidene chloride; and
   (d) separating said chlorinated vinylidene chloride from said 1,1-dichloro-1-fluoroethane solution.

16. The method in accordance with claim 15 including separating by distillation.

17. The method in accordance with claim 15 including adding chlorine to said solution in a mole ratio of 1:1 to 5:1 chlorine to vinylidene chloride.

18. The method in accordance with claim 15 including adding chlorine to said solution in a mole ratio of at least 2.5:1 chlorine to vinylidene chloride.

19. The method in accordance with claim 15 including contacting effected in a temperature range of 0° to 100° C.

20. The method in accordance with claim 15 including contacting effected in a temperature range of 10° to 60° C.

21. The method in accordance with claim 15 including conditioning said alumina prior to effecting chlorination by treating said alumina with chlorine.

22. The method in accordance with claim 8 including conditioning said alumina by contacting with a 1,1-dichloro-1-fluoroethane solution containing chlorine.

23. The method in accordance with claim 15 wherein said vinylidene chloride in said solution is reduced to less than 200 ppm.

24. The method in accordance with claim 15 wherein said vinylidene chloride in said solution is reduced to less than 100 ppm.

25. The method in accordance with claim 15 wherein said contacting is for a period of less than 2 hours.

26. The method in accordance with claim 15 wherein the alumina support has a surface area in the range of 80 to 350 $m^2/g$.

27. The method in accordance with claim 1 including maintaining water in said solution in the range of 20 to 3000 ppm.

* * * * *